(12) United States Patent
Kim et al.

(10) Patent No.: US 11,905,317 B2
(45) Date of Patent: Feb. 20, 2024

(54) BEE VENOM-PURIFYING METHOD COMPRISING VIRAL CLEARANCE PROCESS AND COMPOSITION FOR PREVENTING OR TREATING INFLAMMATORY DISEASE BY USING SAME

(71) Applicant: UBIO INC., Seoul (KR)

(72) Inventors: Keun Nam Kim, Seoul (KR); Gun Won Bae, Uiwang-si (KR); Jee Sun Hwang, Anseong-si (KR); Sun Myung Yoon, Seoul (KR)

(73) Assignee: UBIO INC., Seoul (KR)

( * ) Notice: Subject to any disclaimer, the term of this patent is extended or adjusted under 35 U.S.C. 154(b) by 472 days.

(21) Appl. No.: 17/311,035

(22) PCT Filed: Dec. 5, 2019

(86) PCT No.: PCT/KR2019/017079
§ 371 (c)(1),
(2) Date: Jun. 4, 2021

(87) PCT Pub. No.: WO2020/116952
PCT Pub. Date: Jun. 11, 2020

(65) Prior Publication Data
US 2022/0024997 A1    Jan. 27, 2022

(30) Foreign Application Priority Data

Dec. 5, 2018 (KR) .......... 10-2018-0155168
May 31, 2019 (KR) .......... 10-2019-0064231

(51) Int. Cl.
*C07K 14/435* (2006.01)
*A61P 29/00* (2006.01)
*A61K 8/64* (2006.01)
*A61K 8/98* (2006.01)
*A61K 38/17* (2006.01)
*A61Q 19/00* (2006.01)

(52) U.S. Cl.
CPC .......... *C07K 14/43572* (2013.01); *A61K 8/64* (2013.01); *A61K 8/987* (2013.01); *A61K 38/1767* (2013.01); *A61P 29/00* (2018.01); *A61Q 19/00* (2013.01)

(58) Field of Classification Search
CPC .......................... C07K 1/34; C07K 14/43572
See application file for complete search history.

(56) References Cited

U.S. PATENT DOCUMENTS

2008/0248127 A1    10/2008    Kim

FOREIGN PATENT DOCUMENTS

| DE | 3017683 A1 * | 11/1980 |
|---|---|---|
| KR | 10-0483496 B1 | 4/2003 |
| KR | 10-2010-0125991 A | 12/2010 |
| KR | 10-2013-0109742 A | 10/2013 |
| KR | 10-2016-0122094 A | 10/2016 |

* cited by examiner

*Primary Examiner* — Qiuwen Mi
(74) *Attorney, Agent, or Firm* — Maschoff Brennan

(57) ABSTRACT

The present invention relates to a bee venom-purifying method comprising a virus clearance process and a composition for preventing or treating inflammatory disease by using same, the method comprising the steps of: (a) preparing a bee venom solution containing bee venom; (b) adjusting the pH of the bee venom solution prepared in step (a) into 2.0 to 4.0 by acid treatment to primarily deactivate viruses; and (c) filtering the pH-adjusted bee venom solution of step (b) through a nanofilter of 10 to 20 nm to secondarily remove viruses.

12 Claims, 9 Drawing Sheets

BEE VENOM-PURIFYING METHOD COMPRISING VIRAL CLEARANCE PROCESS AND COMPOSITION FOR PREVENTING OR TREATING INFLAMMATORY DISEASE BY USING SAME

FIELD OF INVENTION

The present invention relates to a method for purification of bee venom, which includes a virus clearance process, and a composition for prevention or treatment of inflammatory diseases using the same.

BACKGROUND OF INVENTION

Bee venom is known to have strong antibacterial and anti-inflammatory effects and has been used in oriental medicine for diseases such as arthritis and gout. The main component of bee venom is melittin, which is a peptide component and is known to have anti-inflammatory and antibacterial action, strong analgesic action, and immune enhancement. In order to use such bee venom as a medicine, virus clearance is necessarily performed during the purification process of bee venom.

In the case of animal-derived medicines, a reason why verification of a virus clearance process is essential is that experimental confirmation of whether the medicine has been designed to effectively remove or inactivate infectious viruses possibly existing in animal organs or tissues is required. This is because it is intended to eliminate viral infection and potential risks caused by viruses that do not die but are introduced into the body in a process of manufacturing animal-derived medicines.

According to animal-derived drug virus safety assessment guidelines, the virus clearance process may be divided into a method of mechanically separating the virus and a method of reducing infectivity by chemical or physical treatment. The method of mechanically separating viruses may include ultra-filtration, chromatography, cold ethanol fraction, etc., and the method of reducing infectivity by chemical or physical treatment may include strong acid treatment, gamma ray irradiation, heat treatment, S/D treatment, and the like.

However, if the virus clearance process is simply applied to the purification method of bee venom as described above, there is a problem of affecting a content of the main physiologically active substance present in bee venom, and research on substantial elimination of such a problem as described above is still needed.

SUMMARY OF INVENTION

Technical Problem to be Solved

According to the present invention, without affecting a content of the main physiologically active substance in the bee venom, there is provided a method for effectively removing viruses, proteins and other impurities which includes: (a) preparing a bee venom solution containing bee venom; (b) firstly, inactivating the virus by adjusting pH of the bee venom prepared in step (a) to 2.0 to 4.0 through acid treatment; and (c) secondly, removing the virus by filtering the pH-adjusted bee venom in step (b) through a nano-filter of 10 to 20 nm, thereby providing a bee venom purification method including a virus clearance process.

However, the technical problem to be solved by the present invention is not limited to the above mentioned problems, and other problems not mentioned herein will be clearly understood and overcome from the following description by those skilled in the art.

Technical Solution

Therefore, the present invention provides a method for purification of bee venom along with a virus clearance process, which includes: (a) preparing a bee venom solution containing bee venom; (b) firstly, inactivating the virus by adjusting pH of the bee venom solution prepared in step (a) to 2.0 to 4.0 through acid treatment; and (c) secondly, removing the virus by filtering the pH-adjusted bee venom solution in step (b) through a nano-filter of 10 to 20 nm.

In step (a), the bee venom solution may further include at least one carbon-based adsorbent selected from the group consisting of activated carbon nanotubes and carbon fibers.

Through the acid treatment in step (b), viruses including bovine viral diarrhea virus (BVDV) or zika virus (ZIKV) may be firstly inactivated.

The acid treatment in step (b) may be performed by treating the bee venom solution with strong acid at a concentration of 0.1 to 1.0 M for 1 to 20 hours.

In the step (b), the pH-adjusted bee venom solution may maintain a melitt in content of 45% by weight ("wt. %") or more.

Before step (c), a step of filtering the pH-adjusted bee venom solution in step (b) through a membrane filter of 0.05 to 1 μm may further be included.

Through the nano-filter in step (c), a virus including at least one selected from the group consisting of bovine viral diarrhea virus (BVDV), zika virus (ZIKV), porcine parvovirus (PPV) and baculovirus (BACV) is secondly removed.

In step (c), the nano-filter may be made of polyether sulfone (PES).

The bee venom solution filtered in step (c) may have a filtration rate of 600 mL/hr or higher or a yield of 60% or higher while maintaining both the melitt in and protein contents of 45 wt. % or more.

After step (c), (d) filtering the bee venom solution filtered in step (c) through a 0.1-1 μm sterile filter; and (e) freeze-drying the bee venom solution filtered in step (d) may be further included.

In one embodiment of the present invention, there is provided a pharmaceutical composition for preventing or treating inflammatory diseases, which includes bee venom prepared by the above method as an active ingredient.

In another embodiment of the present invention, there is provided a cosmetic composition for preventing or improving inflammatory diseases, which includes bee venom prepared by the above method as an active ingredient.

Effect of Invention

The purification method of bee venom along with a virus clearance process according to the present invention essentially includes adjusting pH of a bee venom solution to 2.0 to 4.0 through acid treatment and filtering the bee venom solution through a nano-filter of 10 to 20 nm, whereby various impurities such as BVDV, ZIKV, PPV and BACV and other impurities can be efficiently removed with high filtration rate and yield without affecting contents of main bioactive substances of bee venom.

Therefore, the bee venom prepared by the method of the present invention is useful as a composition for preventing, improving or treating inflammatory diseases.

BRIEF DESCRIPTION OF DRAWINGS

FIG. 7 shows the results of observing morphological changes (i.e., cytopathic effects (CPF)) for verification of the virus clearance process with regard to the method of manufacturing bee venom along with the virus clearance process according to Example 4, when virus spike before the acid treatment was induced and virus cultured cells were treated with the bee venom after nano-filtration process, as shown in FIGS. 6(a) and (b).

BEST MODE

Figure 1A:
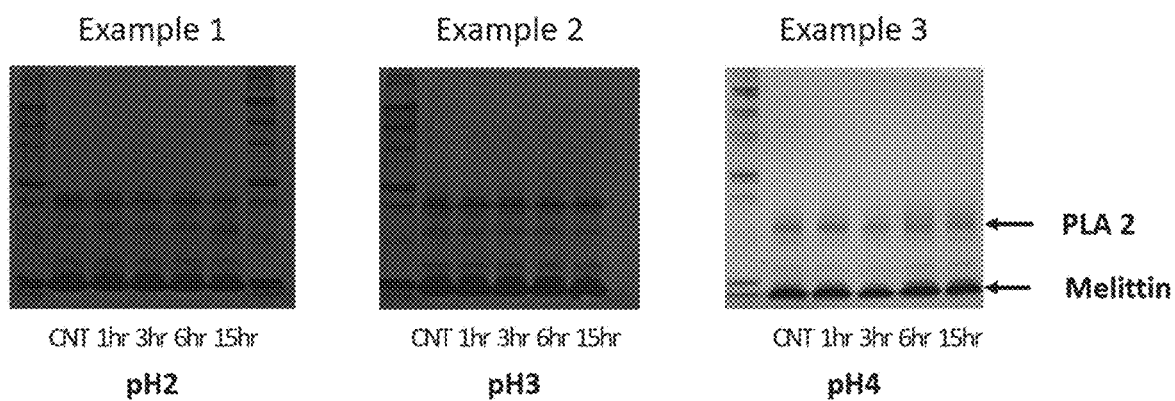
FIGS. 1(a) and (d) show the results of electrophoresis and HPLC analysis of the bee venom prepared in Examples 1 to 3.
Figure 1B:
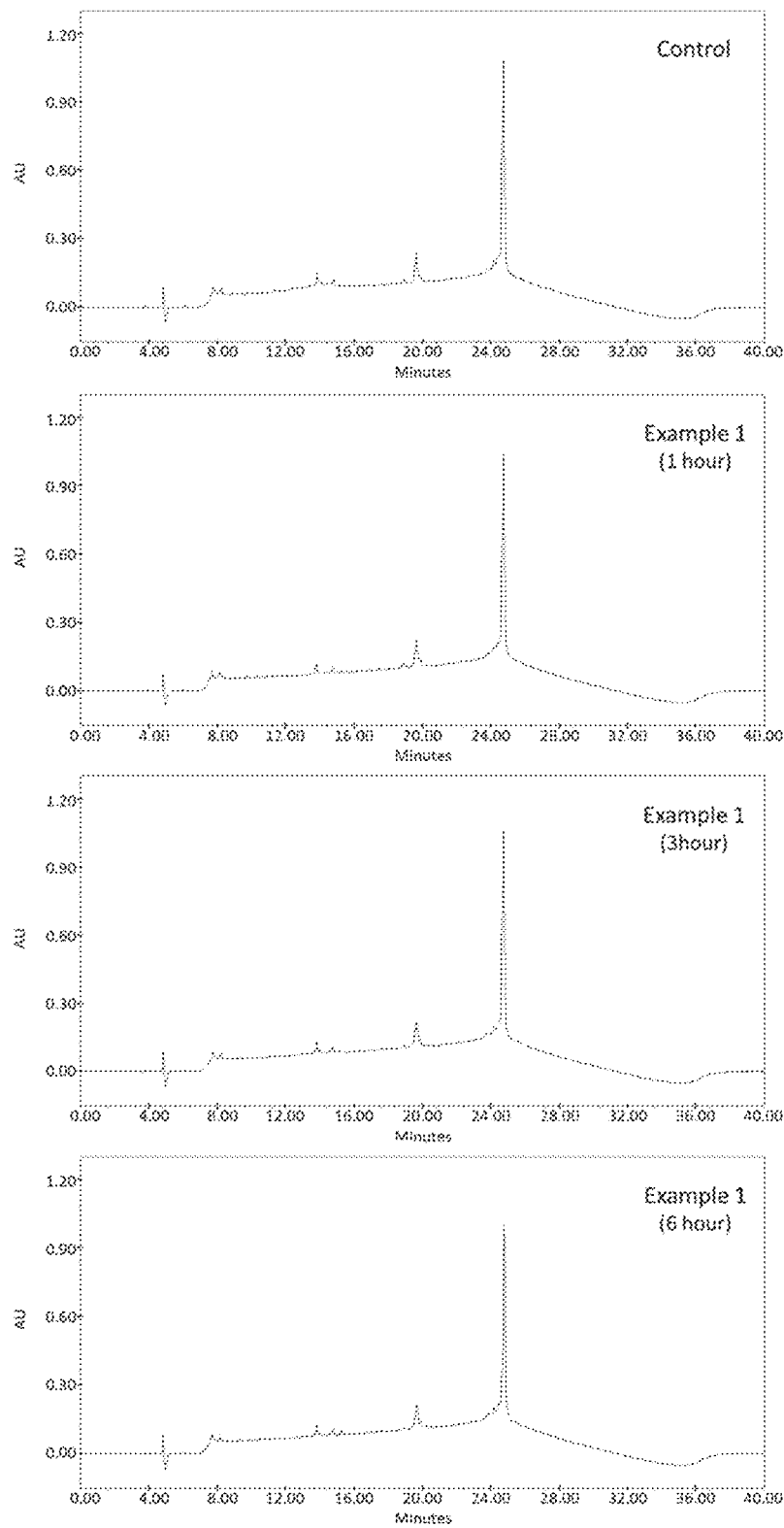
Figure 1C:
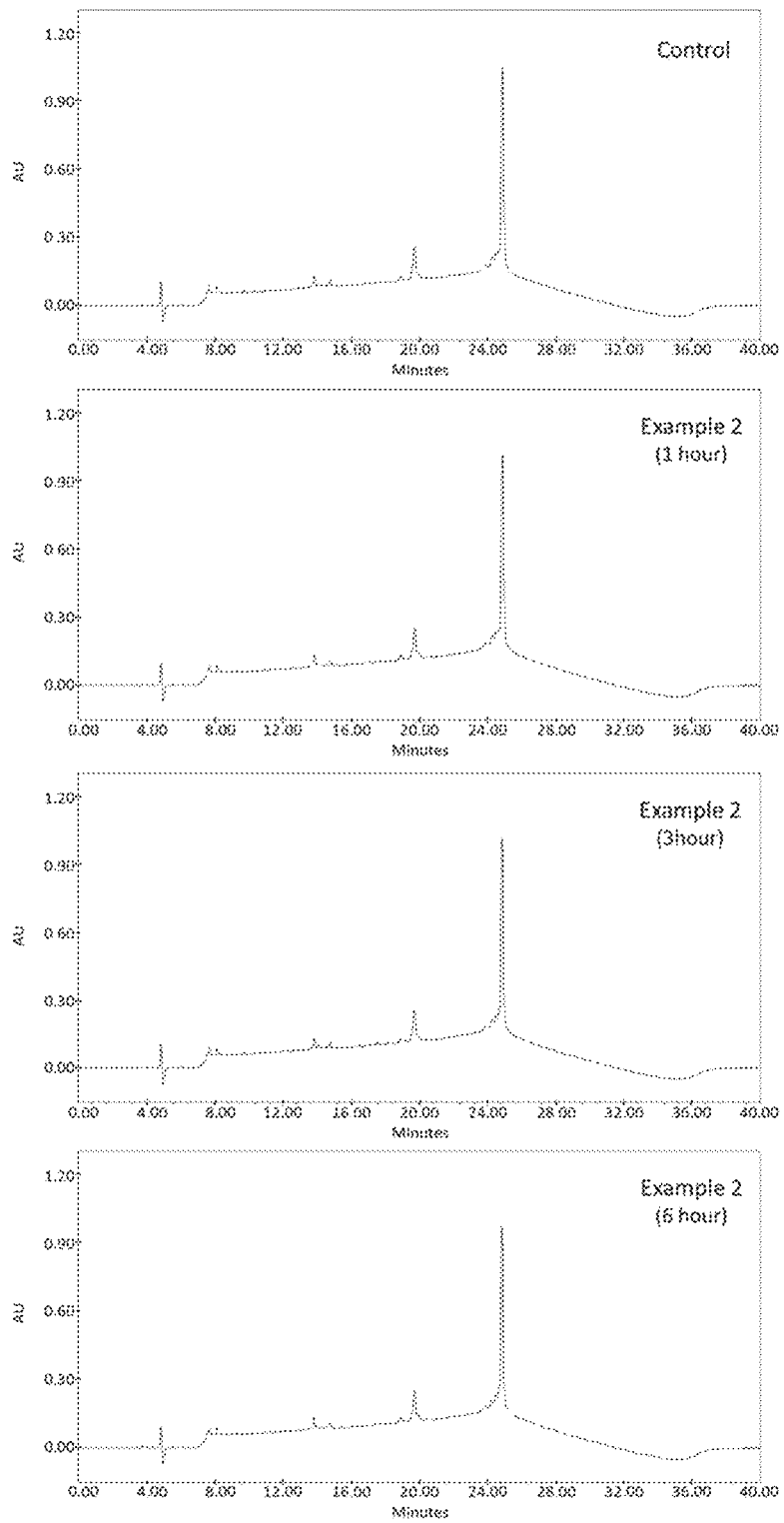
Figure 1D:
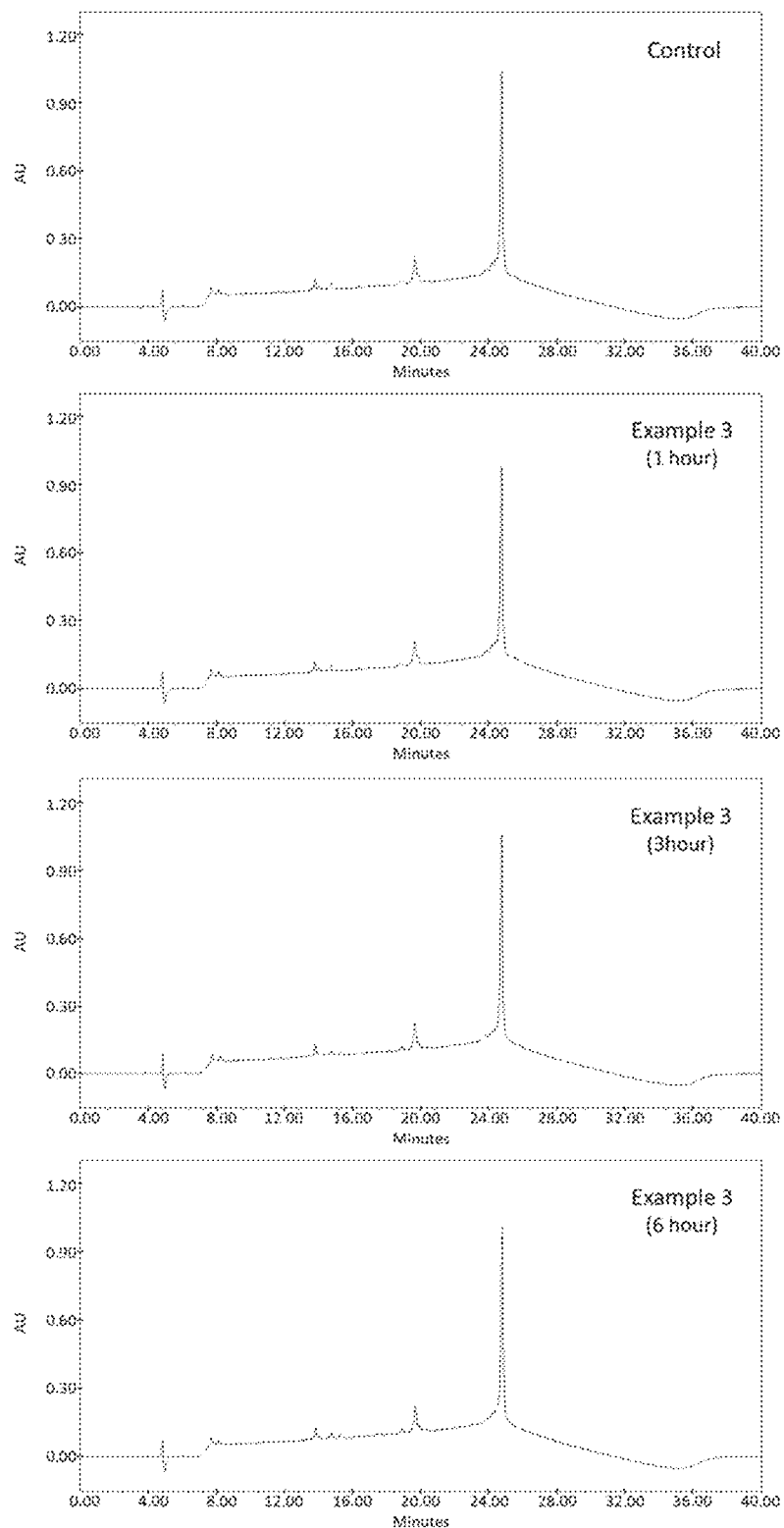

The present inventors studied a method of effectively removing various impurities such as BVDV, ZIKV, PPV and BACV, and other impurities without affecting contents of main bioactive substances in bee veno mand found improved effects by optimizing acid treatment and combining the same with a filter process, thereby completing the present invention.

Hereinafter, the present invention will be described in detail.

Purification of Bee Venom Along with Virus Clearance Process

The present invention provides a method for purification of bee venom along with a virus clearance process, which includes: (a) preparing a bee venom solution containing bee venom; (b) firstly, inactivating virus by adjusting the pH of the bee venom solution prepared in step (a) to 2.0 to 4.0 through acid treatment; and (c) secondly, removing the virus by filtering the pH-adjusted bee venom solution in step (b) through a nano-filter of 10 to 20 nm.

As used herein, "virus clearance" is a concept that includes both inactivation and removal of a virus, and inactivation of the virus means that viral infectivity is reduced by chemical or physical treatment, while removal of the virus refers to mechanically removing virus particles possibly existing in an animal-derived raw material.

On the other hand, the virus may be divided according to animal-derived host, the presence or absence of a viral envelope, a size of the virus and type of nucleic acid, wherein the virus subjected to virus clearance may include bovine viral diarrhea virus (BVDV), zika virus (ZIKV), porcine parvovirus (PPV) and baculovirus (BACV), or the like.

TABLE 1

| Virus name | Family | Natural host | Envelope | Size (nm) | Nucleic acid |
|---|---|---|---|---|---|
| Bovine Viral Diarrhea Virus (BVDV) | Toga | Cow | Present | 40-60 | RNA |
| Zika virus (ZIKV) | Flavivirus | Mosquito | Present | 40 | RNA |
| Porcine Parvovirus (PPV) | Parvoviridae | Pig | Not present | 18-24 | DNA |
| Baculovirus (BACV) | Baculoviridae | Silkworm | Not present | 280-385 | DNA |

As shown in Table 1, BVDV is a single-strand RNA virus having an envelope and a medium size (about 40 to 60 cm) that exhibits about average resistance to physicochemical inactivation. BVDV has relatively low heat resistance, while being sensitive to organic solvents, unstable in acids but stable in bases. Further, Zika is spherical with a diameter of about 50 nm wherein an icosahedralnucleocapsid is surrounded by an envelope derived from vesicles of the host cell. The envelope includes two types of proteins of M (membrane) and E (envelope), expressed on the envelope, and may have a positive single-stranded RNA of about 11 kb. On the other hand, PPV is a kind of non-lipid-encapsulated DNA virus (icosahedron) and belongs to the parvovirus family (18-24 nm in diameter). Such parvoviruses may withstand extremely high temperatures, are stable in oily solvents and is relatively resistant to acidic pH. In addition, BACV may be a virus specific to invertebrates, especially insects, but this type of virus may also appear in crustaceans. Virus particles contain double-stranded DNA with a molecular weight $(30 \sim 110) \times 10^6$ Daltons, which are rod cells having one or plural nucleocapsids surround by a membrane, and have a size of about $(200\text{-}400) \times (30\text{-}90)$ nm.

First, the purification method of bee venom along with a virus clearance process according to the present invention may include preparing a bee venom solution containing bee venom (step (a)).

Specifically, the bee venom solution may be prepared by completely dissolving bee venom in distilled water or a buffer, so as to reach a content of 0.01 to 20.0 wt. %. When the content of bee venom (raw material) in the bee venom solution is less than 0.01 wt. %, there is a problem that physiological activity effects by bee venom (purified bee venom) corresponding to a final product are too small. On the other hand, when the content of bee venom in the bee venom solution is more than 20.0 wt. %, there is a problem that a purification efficiency of bee venom is lowered.

Further, adding at least one carbon-based adsorbent selected from the group consisting of activated carbon nanotubes and carbon fibers in the bee venom may remove additional impurities and the like.

Then, optionally, the bee venom solution may be filtered through a sterile filter of 0.1 to 1 μm under reduced pressure filtration conditions.

Next, the method for purification of bee venom along with a virus clearance process according to the present invention may include firstly inactivating the virus by adjusting pH of the bee venom solution prepared in step (a) to 2.0 to 4.0 through acid treatment (step (b)).

Specifically, the acid treatment process may firstly inactivate viruses including, for example, bovine viral diarrhea virus (BVDV) or zika virus (ZIKA), while not affecting the content of a main bioactive substance (melittin, phospholipase A2, etc.) in the bee venom. Therefore, through the acid treatment, the pH of the bee venom may be adjusted to 2.0 to 4.0, and the pH is preferably adjusted to 2.5 to 3.5, but is not limited thereto.

More specifically, the acid treatment may be performed by treating the bee venom with a strong acid at a concentration of 0.1 to 1.0 M for 1 to 20 hours. The strong acid may include one or more selected from the group consisting of hydrochloric acid, acetic acid, sulfuric acid, nitric acid and hydrofluoric acid. When the concentration of the strong acid is less than 0.1 M, there is a problem that too much of the strong acid is required in the acid treatment process. If a concentration of the strong acid exceeds 1.0 M, it may affect the main bioactive substances of bee venom. Further, the acid treatment is preferably conducted for 1 to 20 hours, more preferably for 1 to 6 hours, but is not limited thereto. If a time for acid treatment is too short, there is a problem that virus inactivation is not sufficiently performed. Further, when the acid treatment time is too long, there is a problem that the main physiologically active substance is affected while deteriorating pharmacological activity effects.

The pH-adjusted bee venom solution may maintain a melittin content in 40 wt. % or more, and preferably 45 wt. % or more, but is not limited thereto.

Subsequently, pH of the pH-adjusted bee venom may be corrected to 4.5 to 5.5 through treatment with a base. The base treatment may be performed by treating the bee venom with a base such as sodium hydroxide at a concentration of 0.1 to 1.0 M. If the concentration of the base is less than 0.1 M, there is a problem that too much of the base is required for the base treatment process. Further, if the concentration of the base exceeds 1.0 M, it may affect main bioactive substances of bee venom.

Next, the method of the present invention along with a virus clearance process may include filtering the pH-adjusted bee venom solution in step (b) through a nano-filter of 10 to 20 nm to remove the virus (step (c)).

Specifically, the nano-filtration process may be a process of removing a virus including, for example, at least one selected from the group consisting of bovine viral diarrhea virus (BVDV), zika virus (ZIKV), porcine parvovirus (PPV) and baculovirus (BACV) without affecting the contents of main physiologically active substances (melittin, phospholipase A2, apamin, etc.) of the bee venom. In this case, if using an organic solvent instead of the nano-filtration process, there is a problem that yield is considerably reduced and pharmacological activity is also considerably deteriorated.

In particular, the nano-filter used in the nano-filtration process may have a pore diameter of 10 to 20 nm, thereby efficiently removing even small viruses (i.e., bovine viral diarrhea virus (BVDV), zika virus (ZIKV) and porcine parvovirus (PPV)).

A material of the nano-filter may be differently selected, and polyethersulfone (PES) is most preferably used in terms of filtration rate, without limitation thereto.

In step (b), the filtered bee venom solution may have a filtration rate of 600 mL/hr or more or a yield of 60% or more, while maintaining bothmellit in and protein contents at 45 wt. % or more.

Accordingly, before use of the nano-filter, optionally, a step of filtering the pH-adjusted bee venom solution in step (b) through a membrane filter of 0.05 to 1 μm to remove protein beforehand may further be included. In this case, the membrane filter may have a molecular weight cut-off value of 200 kDa.

Thereafter, (d) a step of again filtering the filtered bee venom solution in step (c) through a sterile filter of 0.05 to 1 μm; and (e) a step of freeze-drying (or lyophilizing) the filtered bee venom solution in step (d) may further be included. In this case, the freeze drying (FD) may include rapidly freezing a raw material at a temperature of −40 to −120° C., and then, applying heat at a low temperature in a stepwise manner in a freeze dryer at a vacuum pressure of 0.1 to 0.9 Torr to sublimate solid ice, thereby obtaining a higher quality of dried product than typical drying. More preferably, the freeze drying is conducted with a vacuum degree of 0.2 to 0.5 Torr at a temperature of −80 to −100° C.

Pharmaceutical Composition for Prevention or Treatment of Inflammatory Diseases

The present invention provides a pharmaceutical composition for preventing or treating inflammatory diseases, which includes bee venom prepared by the aforementioned method as an active ingredient.

The bee venom prepared by the above method refers to a state in which viruses, other impurities, and the like are effectively removed while maintaining contents of the main bioactive substances (melittin, phospholipase A2, and apamin) at a certain level or more.

The term "inflammatory disease" in the present specification may include one or more selected from the group consisting of allergies, dermatitis, a topicdermatitis, conjunctivitis, periodontitis, rhinitis, otitis media, sore throat, tonsillitis, pneumonia, gastric ulcer, gastritis, Crohn's disease, colitis, gout, ankylosing spondylitis, rheumatic fever, lupus, fibromyalgia, psoriatic arthritis, osteoarthritis, rheumatoid arthritis, periarthritis, tendinitis, tenosynovitis, peritendinitis, myositis, hepatitis, cystitis, nephritis, Sjogren's syndrome, multiple sclerosis, and acute and chronic inflammatory diseases, but is not limited thereto.

The pharmaceutical composition for prevention or treatment of inflammatory diseases according to the present invention may be formulated and used in the form of oral formulations such as powders, granules, tablets, capsules, suspensions, emulsions, syrups, aerosols, external preparations, suppositories, and sterile injectable solutions, respectively, according to conventional methods. Further, the composition may include a suitable carrier, excipient, or diluent commonly used in the manufacture of pharmaceutical compositions for formulation.

When formulated, the formulation may be manufactured using diluents or excipients such as fillers, weights, binders, wetting agents, disintegrating agents, surfactants, etc., which are usually used in the art.

A preferred dosage of bee venom prepared by the above method in the pharmaceutical composition for prevention or treatment of inflammatory diseases according to the present invention may vary depending on the patient's condition, weight, disease severity, drug form, administration route, and duration, but may be appropriately selected by those skilled in the art. However, for desired effects, the bee venom may be administered at 0.0001 to 2,000 mg/kg per day, preferably 300 to 2,000 mg/kg. Administration may be conducted once a day or several times per day. However, the scope of the present invention is not limited by the dosage.

Cosmetic Composition for Prevention or Improvement of Inflammatory Diseases

The present invention provides a cosmetic composition for preventing or improving inflammatory diseases, which includes bee venom prepared by the aforementioned method as an active ingredient.

The "bee venom prepared by the aforementioned method" and "inflammatory disease" have already been described above, and thus, redundant description will be omitted.

Further, other constitutional components to be added are not particularly limited, and any of the above components may be blended within a range not impairing the objects and effects of the present invention, but those blended at a weight percentage of 0.01 to 5% based on the total weight. Further, the components are more preferably blended at a weight percentage of a 0.01 to 3 wt. %, without being limited thereto.

The cosmetic composition may have the form of a solution, emulsion or viscous mixture, but is not limited thereto.

The components included in the cosmetic composition may include components commonly used in cosmetic compositions in addition to the above compound as an active ingredient, and may include conventional adjuvants such as stabilizers, solubilizers, vitamins, pigments and fragrances, as well as carriers, without being limited thereto.

The cosmetic composition may be prepared in any formulation conventionally manufactured in the art, and may be prepared as an emulsion, cream, lotion, pack, foundation, cosmetic liquid or hair cosmetic material, without being limited thereto. Specifically, the cosmetic composition may include the formulation of skin lotion, skin softener, skin toner, astringent, lotion, milk lotion, moisture lotion, nutrition lotion, massage cream, nutrition cream, moisture cream, hand cream, foundation, essence, nutrition essence, pack, soaps, cleansing foams, cleansing lotions, cleansing creams, body lotion or body cleanser formulations, without being limited thereto.

Furthermore, the present invention provides a use of the bee venom prepared by the aforementioned method in a pharmaceutical composition for prevention or treatment of inflammatory diseases.

Further, the present invention provides a use of the bee venom prepared by the aforementioned method in a cosmetic composition for prevention or treatment of inflammatory diseases.

Further, the present invention provides a method for preventing or treating inflammatory diseases, which includes administering the bee venom prepared by the aforementioned method to an individual.

The "individual" in the present invention means a subject in need of treatment fora disease, and more specifically, mammals such as a human or non-human primate, mouse, rat, dog, cat, horse, and cow, or the like.

As described above, the purification method of bee venom along with a virus clearance process according to the present invention is characterized in that the method essentially includes adjusting pH of the bee venom to 2.0 to 4.0 through acid treatment and filtering the bee venom through a nano-filter of 10 to 20 nm, whereby a variety of viruses such as BVDV, ZIKV, PPV and BACV, other impurities, etc. may be efficiently removed with high filtration rate and yield without affecting contents of main physiologically active ingredients of the bee venom. Specifically, the nano-filter of 10 to 20 nm has an advantage of effectively removing various viruses.

Therefore, the bee venom prepared by the method according to the present invention is useful in a composition for prevention, improvement or treatment of inflammatory diseases.

Hereinafter, preferred embodiments are provided for understanding of the present invention. However, the following examples are only provided to more easily understand the present invention, and the contents of the present invention are not limited by the following examples.

EXAMPLE

Example 1: Acid pH 2 Treatment

Bee venom was added to purified water to completely dissolve the bee venom to reach 5.0 wt. %, there by preparing a bee venom solution. First, the bee venom was filtered through a 0.22 µm pore sterile filter under reduced pressure filtration conditions. Then, the bee venom solution was treated with hydrochloric acid at a concentration of 0.2M for 1 to 5 hours to adjust pH of the bee venom to pH 2, thereby firstly inactivating virus. Then, the solution was treated again with sodium hydroxide at a concentration of 0.2M to adjust the pH of the bee venom to pH 5. Thereafter, the bee venom solution was pre-filtered through a 0.22 µm pore membrane filter under reduced pressure filtration conditions, and then, rapidly frozen at a temperature of −80° C. or lower and lyophilized in a vacuum state of 0.5 torr or less in order to prepare powdered bee venom. At this time, a control group was prepared by freeze-drying without acid treatment.

Example 2: Acid pH 3 Treatment

After adjusting the pH of the bee venom to pH 3 with 0.2M concentration of hydrochloric acid, the bee venom was treated for 1 to 15 hours. The bee venom was prepared in the same manner as in Example 1, except that the pH of the bee venom was adjusted to pH 2.

Example 3: Acid pH 4 Treatment

After adjusting the pH of the bee venom to pH 4 with 0.2M hydrochloric acid, the bee venom was treated for 1 to 15 hours. The bee venom was prepared in the same manner as in Example 1, except that the pH of the bee venom was adjusted to pH 4.

Experimental Example 1: Optimization of Acid Treatment Process

Protein contents of the bee venom prepared in Examples 1 to 3 were analyzed by electrophoresis and HPLC, and the results are shown in Table 2 and FIGS. 1(a) to (d).

TABLE 2

| Section | pH | Pre-treatment time | Content of melittin (%) |
|---|---|---|---|
| Control (CNT) | 5.03 | | 50.14 |
| Example 1 | 2 | 1 hour | 49.45 |
| | | 3 hours | 47.28 |
| | | 6 hours | 45.90 |
| | | 15 hours | 40.43 |
| Example 2 | 3 | 1 hour | 50.66 |
| | | 3 hours | 49.72 |
| | | 6 hours | 47.68 |
| | | 15 hours | 46.51 |
| Example 3 | 4 | 1 hour | 50.23 |
| | | 3 hours | 49.53 |
| | | 6 hours | 47.01 |
| | | 15 hours | 46.78 |

As shown in Table 2, when the acid treatment pH was too low, as in Example 1, there was a problem in that the melittin content was significantly reduced. As in Examples 2 to 3, it was confirmed that the acid treatment pH is preferably 3 to 4. Further, when the acid treatment time was too long, there was a problem in that the melittin content was significantly reduced. Therefore, it was confirmed that the acid treatment time was preferably maintained for 1 hour to 15 hours, especially 1 hour to 6 hours.

Experimental Example 2: Pharmacological Activity Effect by Optimization of Acid Treatment Process (1) Raw264.7 Cytotoxicity Evaluation The macrophage cell line, Raw264.7 cells, was purchased from the Korean Cell Line Bank (Cat No. KCLB40071) and used. Further, the experiment was implemented by culturing the above macrophages in an incubator at 37° C. with 5% $CO_2$, using Dulbecco's modified Eagle medium (DMEM, Hyclone) including 10% fetal bovine serum (FBS, Hyclone), 100 IU/ml penicillin and 100 μg/ml streptomycin.

Figure 2:
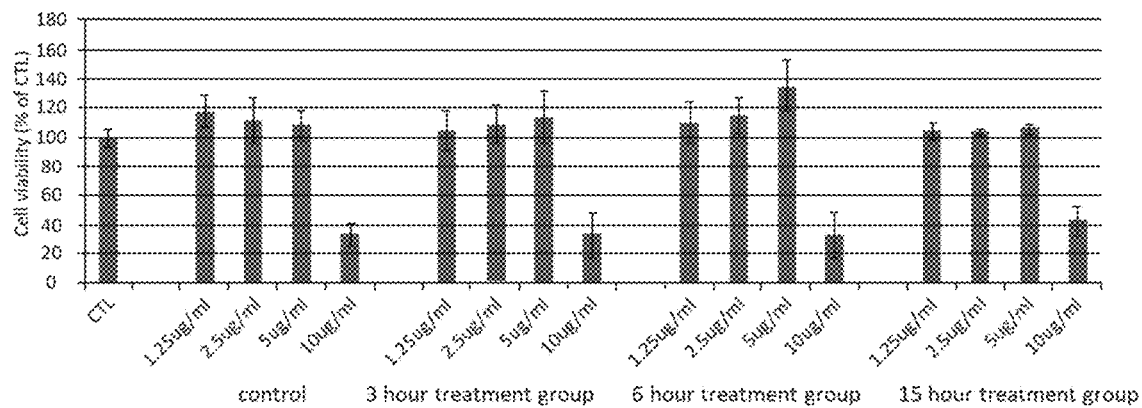
FIG. 2 shows the results of evaluation of Raw264.7 cytotoxicity of the bee venom prepared in Example 2 or bee venom (raw material).

After culturing RAW264.7 macrophages, bee venom was added at pH 3 in Example 2 and at each of four (4) concentrations by treatment times. Thereafter, in order to confirm cell viability, reaction with MTT (methylthiazol tetrazolium bromide, Sigma Aldrich) was performed. After seeding cells in each well of a 24 well plate (BD, Falcon) ($5 \times 10^4$/well), the samples were treated in relation to concentrations and cultured in a 37° C. incubator for 48 hours, followed by determining cell viability. After reacting the product with MTT solution (3-(4,5-dimethylthiazol-2-yl)-2, 5-diphenyl tetrasodium bromide) for 4 hours, 400 μl of DMSO was added thereto in order to dissolve insoluble formazan crystals, followed by measuring absorbance at 570 nm wavelength using an ELISA plate reader (TECAN, Infinite M200 pro). Measured results are shown in Table 3 and FIG. 2.

As shown in Table 3, it was confirmed that the bee venom prepared in Example 2 or bee venom (raw material) exhibited non-toxicity at an amount of up to 5 μg/ml, regardless of the acid treatment time.

(2) Nitric Oxide Release Measurement

To measure nitric oxide release, the macrophages, that is, raw264.7 cells were dispensed and cultured in a 48 well plate to reach $2.5 \times 10^4$/well. Subsequently, in order to confirm a nitric oxide inhibitory rate of the bee venom, the product was treated in relation to concentration and incubated for 24 hours. After incubation, LPS at a concentration of 1 μg/mL was added to each well, followed by culturing for 24 hours. After culturing, 100 μL of the culture supernatant was taken and then the same amount of Griess reagent was added and left for 15 minutes, followed by measuring absorbance at 540 nm wavelength using an ELISAp late reader (TECAN, Infinite M200 pro). Results thereof are shown in Table 3.

At this time, among the samples used, the control group was prepared by a freeze-drying process without acid treatment of bee venom in order to compare the nitric oxide release activity before and after acid treatment of purified bee venom.

As shown in Table 3, with regard to the control group as well as the purified bee venom samples treated for 3 hours, 6 hours and 15 hours, respectively, at pH3 of Example 2, it was confirmed that NO inhibitory rate levels were substantially similar in all of the samples. This means that the acid treatment process of purified bee venom in the purification method of bee venom does not significantly affect the nitric oxide release activity of the purified bee venom.

(3) Inflammatory TNF-Alpha Measurement

To measure TNF-alpha, the macrophages, that is, raw264.7 cells, were dispensed and cultured in a 48 well plate to reach $2.5 \times 10^4$/well. Subsequently, in order to confirm TNF-alpha of the bee venom, the product was treated with different concentrations and incubated for 24 hours. After incubation, LPS at a concentration of 1 μg/mL was added to each well, followed by culturing for 24 hours. After culturing, the supernatant was taken and subjected to measurement of TNF-alpha by means of a Quantikine ELISA Kit (R&D Systems; MTA00B). Further, for cell quantification, the supernatant was removed and then the remaining product was reacted for 4 hours using MMT solution (3-(4,5-dimethylthiazol-2-yl)-2,5-diphenyl tetrasodium bromide). After the reaction, 300 μl of DMSO was added thereto to dissolve insoluble formazan crystals, followed by measuring absorbance at 570 nm wavelength using an ELIASA plate reader (TECAN, Infinite M200 pro). Measured results are shown in Table 3.

At this time, among the samples used, the control group was prepared by a freeze-drying process without acid treatment of bee venom in order to compare TNF-alpha inhibitory activity before and after acid treatment of purified bee venom.

As shown in Table 3, the sample subjected to acid treatment for 6 hours or less exhibited TNF-alpha inhibitory activity substantially equal to that of the control group subjected to a freeze-drying process without acid treatment. On the contrary, when the acid treatment time was 15 hours, TNF-alpha inhibitory activity was demonstrated to be deteriorated as compared to the control group. This means that, if the acid treatment time in the purification method of bee venom is set to be within 6 hours, the acid treatment process does not affect TNF-alpha activity of purified bee venom.

TABLE 3

| | | Concentration | Control | Treatment group survived for 3 hours | Treatment group survived for 6 hours | Treatment group survived for 15 hours |
|---|---|---|---|---|---|---|
| Test concentration set | Cytotoxicity (Raw264.7) | Up to 5 μg/ml, non-toxicity confirmed | Up to 5 μg/ml, non-toxicity confirmed | Up to 5 μg/ml, non-toxicity confirmed | Up to 5 μg/ml, non-toxicity confirmed | Up to 5 μg/ml, non-toxicity confirmed |
| Anti-inflammation confirmed | No activity inhibition | 1.25 μg/ml | 27% | 24% | 21% | 22% |
| | | 2.5 μg/ml | 29% | 27% | 24% | 23% |
| | | 5.0 μg/ml | 31% | 32% | 28% | 30% |
| | TNF-alpha inhibition ability | 1.25 μg/ml | 12% | 13% | 10% | 9% |
| | | 2.5 μg/ml | 25% | 27% | 25% | 14% |
| | | 5.0 μg/ml | 40% | 38% | 34% | 21% |

Example 4: Use of Nano-Filter (PES)

The bee venom was added to purified water to completely dissolve the bee venom to reach 5.0 wt. %, thereby preparing a bee venom solution. At this time, activated carbon may be used to remove foreign substances and odors. Thereafter, the bee venom was filtered through a 0.22 μm pore sterile filter under reduced pressure filtration conditions. Then, the bee venom solution was treated with hydrochloric acid at a concentration of 0.2M for 3 hours to adjust pH of the bee venom to pH 3, thereby firstly inactivating virus. Then, the bee venom solution was treated again with sodium hydroxide at a concentration of 0.2M to adjust the pH of the bee venom to pH 5. At this time, the pH may be corrected through ultrafiltration (UF) instead of using sodium hydroxide. Subsequently, the bee venom was pre-filtered through a membrane filter of 0.1 μm pores under reduced pressure filtration conditions, followed by filtration using a polyethersulfone (PES) material nano-filter with 20 nm pores (VirosartCPV, Sartorius). Specifically, after mounting the nano-filter on a filtration device, 10 ml of ultrapure water was poured in a sample container and pressure was applied using nitrogen gas to remove air bubbles. After removing the bubbles from the nano-filter pores, the bee venom solution was added to the sample container and filtered using nitrogen gas under pressure. At this time, the pressure was maintained at 2.0 to 3.0 bar. Thereafter, the bee venom solution was filtered again through a 0.22 μm pore sterile filter under reduced pressure filtration conditions, followed by rapidly freezing at a temperature of −80° C. or lower and freeze-drying the same in a vacuum of 0.5 torr or less so as to produce bee venom in powder form.

At this time, the control group was prepared by freeze-drying without acid treatment and nano-filtration.

Example 5: Use of Nano-Filter (PVDF)

The bee venom was prepared in the same manner as in Example 4, except that a polyethersulfone (PES) material nano-filter (VirosartCPV, Sartorius) was replaced by a polyvinylidene fluoride (PVDF) material nano-filter.

Experimental Example 3: Optimization of Nano-Filtration Process (1)

Figure 3A:
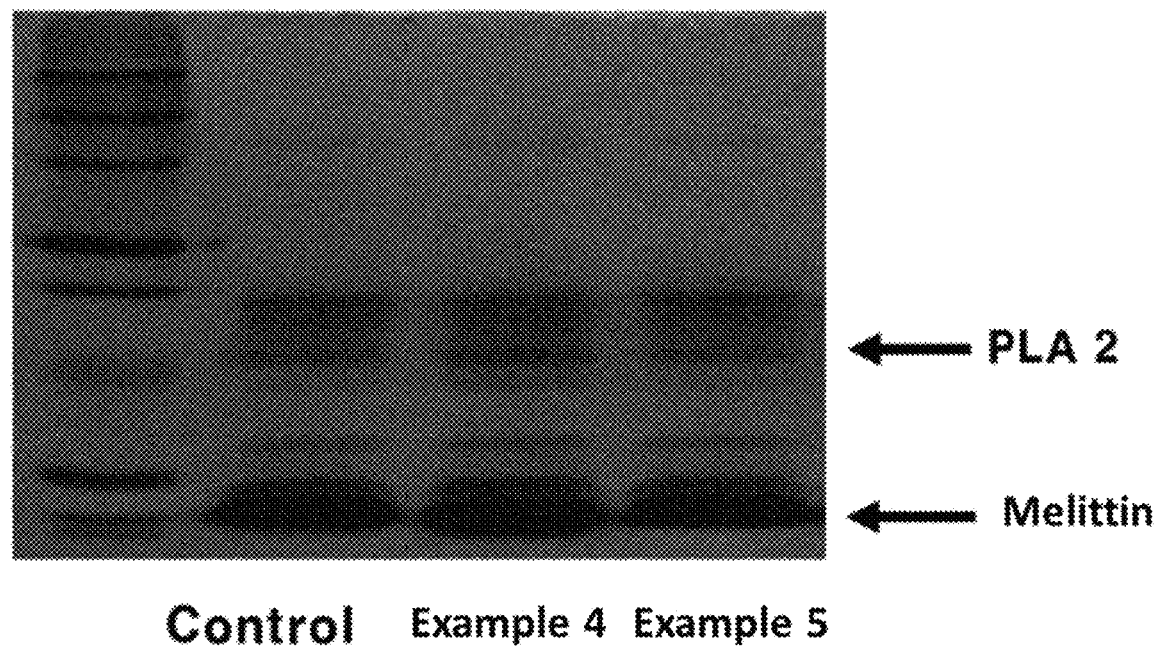
FIGS. 3(a) and (b) show the results of electrophoresis and HPLC analysis of the bee venom prepared in Examples 4 to 5.
Figure 3B:
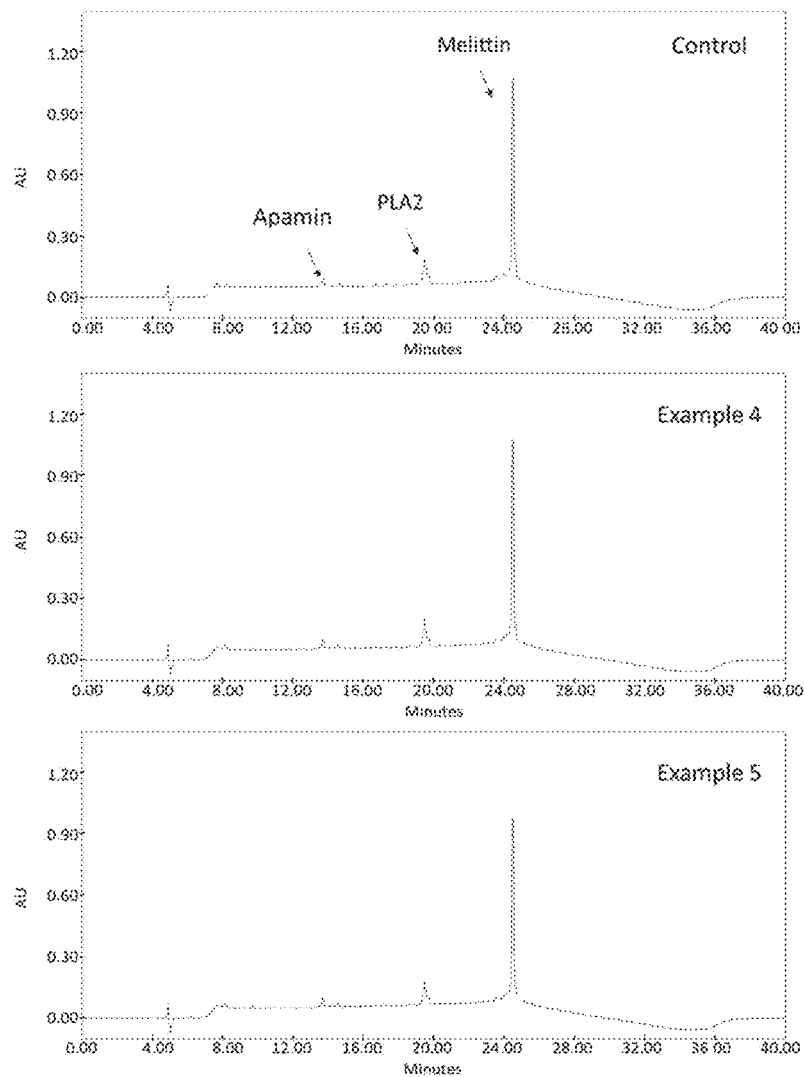

Protein content and filtration rate of the bee venom prepared in Examples 4 to 5 were analyzed by electrophoresis and HPLC, and the results thereof are shown in Table 4, FIGS. 3(a) and 3(b).

TABLE 4

| Section | Content of melittin | Content of protein | Filtration rate |
| --- | --- | --- | --- |
| Control | 63.90% | 61.28% | — |
| Example 4 (PES) | 61.82% | 60.94% | 700 mL/hr |
| Example 5 (PVDF) | 63.04% | 60.04% | 315 mL/hr |

As shown in Table 4, it was confirmed that the melittin content and protein content of the bee venom are substantially similar in all samples after the nano-filtration process, regardless of the material of the nano-filter. Therefore, it is understood that the nano-filtration process does not affect the main component content of bee venom. In particular, in the case of the polyether sulfone (PES) material nano-filter as in Example 4, it was confirmed that the filtration rate is superior to the polyvinylidene fluoride (PVDF) material nano-filter as in Example 5.

Comparative Example 1: Use of Organic Solvent

The bee venom was added to purified water to completely dissolve the bee venom to reach 5.0 wt. %, thereby preparing a bee venom solution. First, the bee venom was filtered through a 0.22 μm pore sterile filter under reduced pressure filtration conditions. Then, the bee venom solution was treated with hydrochloric acid at a concentration of 0.2M for 3 hours to adjust pH of the bee venom to pH 3, thereby firstly inactivating virus. Then, the bee venom solution was treated again with sodium hydroxide at a concentration of 0.2M to adjust the pH of the bee venom to pH 5. Thereafter, the bee venom solution was poured in 70% ethanol to precipitate the same and left at room temperature for 1 hour, followed by adding purified water under stirring. Next, ethanol was removed by filtration through an ultrafiltration membrane of 3 kDa or less and concentration. Subsequently, the bee venom solution was filtered again through a 0.22 μm pore sterile filter under reduced pressure filtration conditions, rapidly frozen at −80° C. or lower followed by freeze-drying the same under a vacuum condition of 0.5 torr or less, thereby preparing bee venom in powder form.

At this time, the control group was prepared by freeze-drying without acid treatment and addition of an organic solvent.

Experimental Example 4: Optimization of Nano-Filtration Process (2)

Figure 4A:
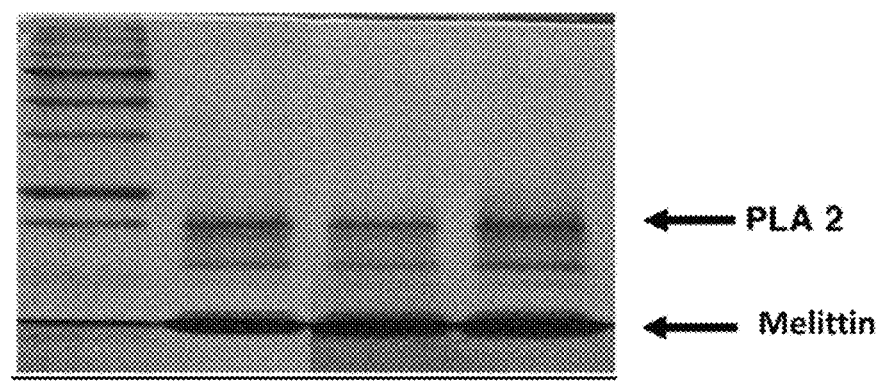
FIGS. 4(a) and (b) show the results of electrophoresis and HPLC analysis of the bee venom prepared in Example 4 and Comparative Example 1.
Figure 4B:
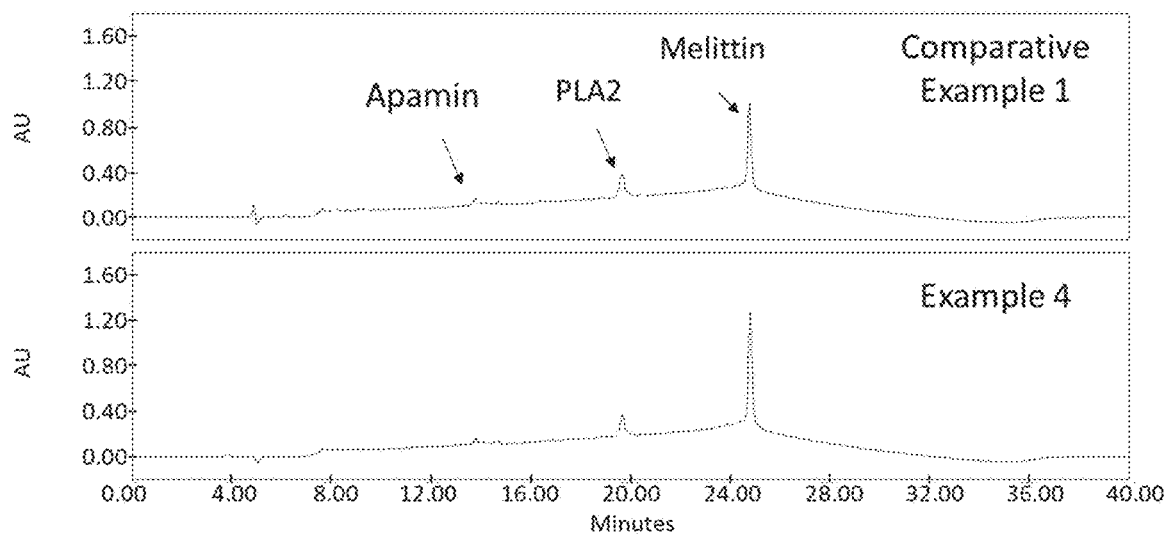
Figure 5:
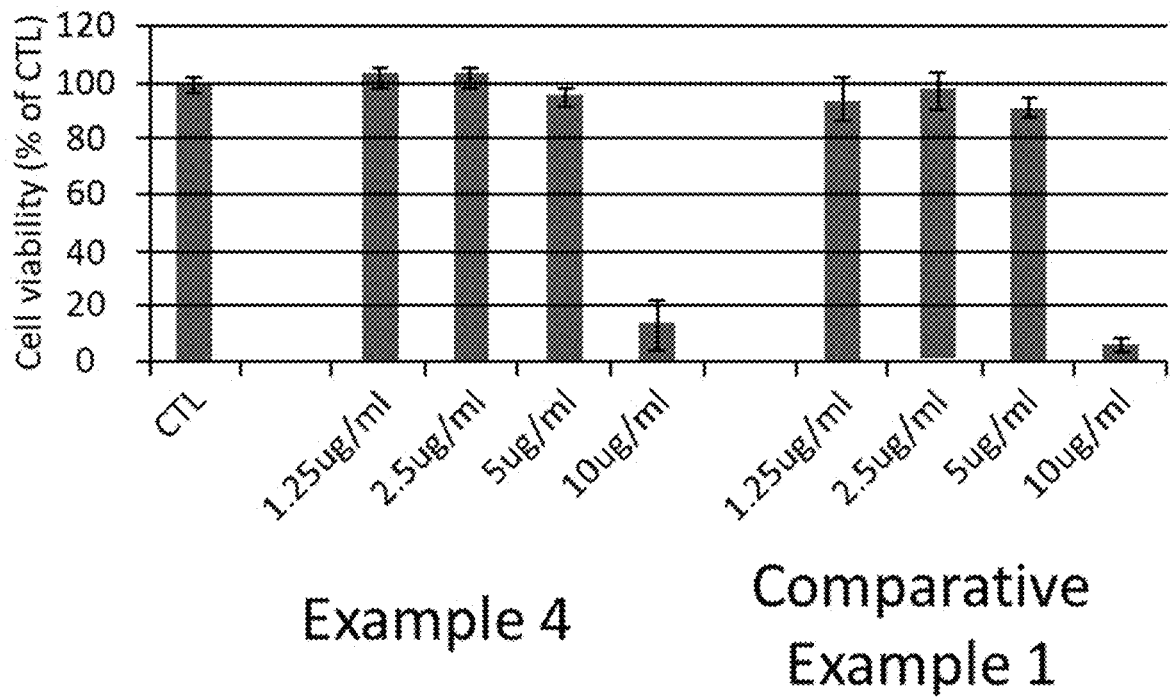
FIG. 5 shows the results of evaluation of Raw264.7 cytotoxicity of the bee venom prepared in Example 4 and Comparative Example 1.

Protein contents and yields of the bee venom prepared in Example 4 and Comparative Example 1 were analyzed by electrophoresis and HPLC, and results thereof are shown in Table 5 and FIGS. 4(a) and (b).

TABLE 5

| Section | Content of melittin | Content of protein | Yield |
| --- | --- | --- | --- |
| Example 4 (nano-filter) | 62.59% | 60.11% | 75.10% |
| Comparative Example 1 (ethanol) | 72.59% | 64.42% | 49.69% |

As shown in Table 5, in the case of Example 4 and Comparative Example 1, the melittin content and protein content of bee venom were found to be similar in both of these examples. However, when using an organic solvent as in Comparative Example 1, yield was significantly lowered.

Experimental Example 5: Pharmacological Activity Effect by Optimization of Nano-Filtration Process (1) Raw264.7 Cytotoxicity Evaluation The same procedure as in Raw264.7 cytotoxicity evaluation of Experimental Example 4 was carried out, and results thereof are shown in Table 6.

As shown in Table 6, it was confirmed that the bee venom prepared in Example 4 and Comparative Example 1 is non-toxic in an amount of up to 5 μg/ml.

(2) Nitric Oxide Release Measurement

The same procedure as the nitric oxide release measurement of Experimental Example 4 was carried out, and results thereof are shown in Table 6.

As shown in Table 6, the bee venom prepared in Example 4 and Comparative Example 1 all exhibited significant NO activity inhibition, and it was confirmed that the activity inhibition level is substantially equal in both processes.

(3) Inflammatory TNF-Alpha Measurement

The same procedure as the inflammatory TNF-alpha measurement of Experimental Example 4 was carried out, and results thereof are shown in Table 6.

As shown in Table 6, the bee venom prepared in Example 4 showed a concentration-independent concentration of TNF-alpha inhibitory activity which is substantially equal to that of the control group. On the contrary, in the case of the bee venom prepared in Comparative Example 1, it was confirmed that the TNF-alpha inhibitory ability is less active than the control group.

TABLE 6

|  |  | Concentration | Control | Example 4 (acid -> nano-filter) | Comparative Example 1 (acid -> organic solvent) |
| --- | --- | --- | --- | --- | --- |
| Test concentration set | Cytotoxicity (Raw264.7) | — | Up to 5 µg/ml, non-toxicity confirmed | Up to 5 µg/ml, non-toxicity confirmed | Up to 5 µg/ml, non-toxicity confirmed |
| Anti-inflammation confirmed | No activity inhibition | 1.25 µg/ml | 27% | 25% | 13% |
|  |  | 2.5 µg/ml | 29% | 26% | 19% |
|  |  | 5.0 µg/ml | 31% | 36% | 48% |
|  | TNF-alpha inhibition ability | 1.25 µg/ml | 12% | 29% | 24% |
|  |  | 2.5 µg/ml | 25% | 36% | 29% |
|  |  | 5.0 µg/ml | 40% | 40% | 31% |

Experimental Example 6: Verification of Virus Clearance Process

Figure 6A:
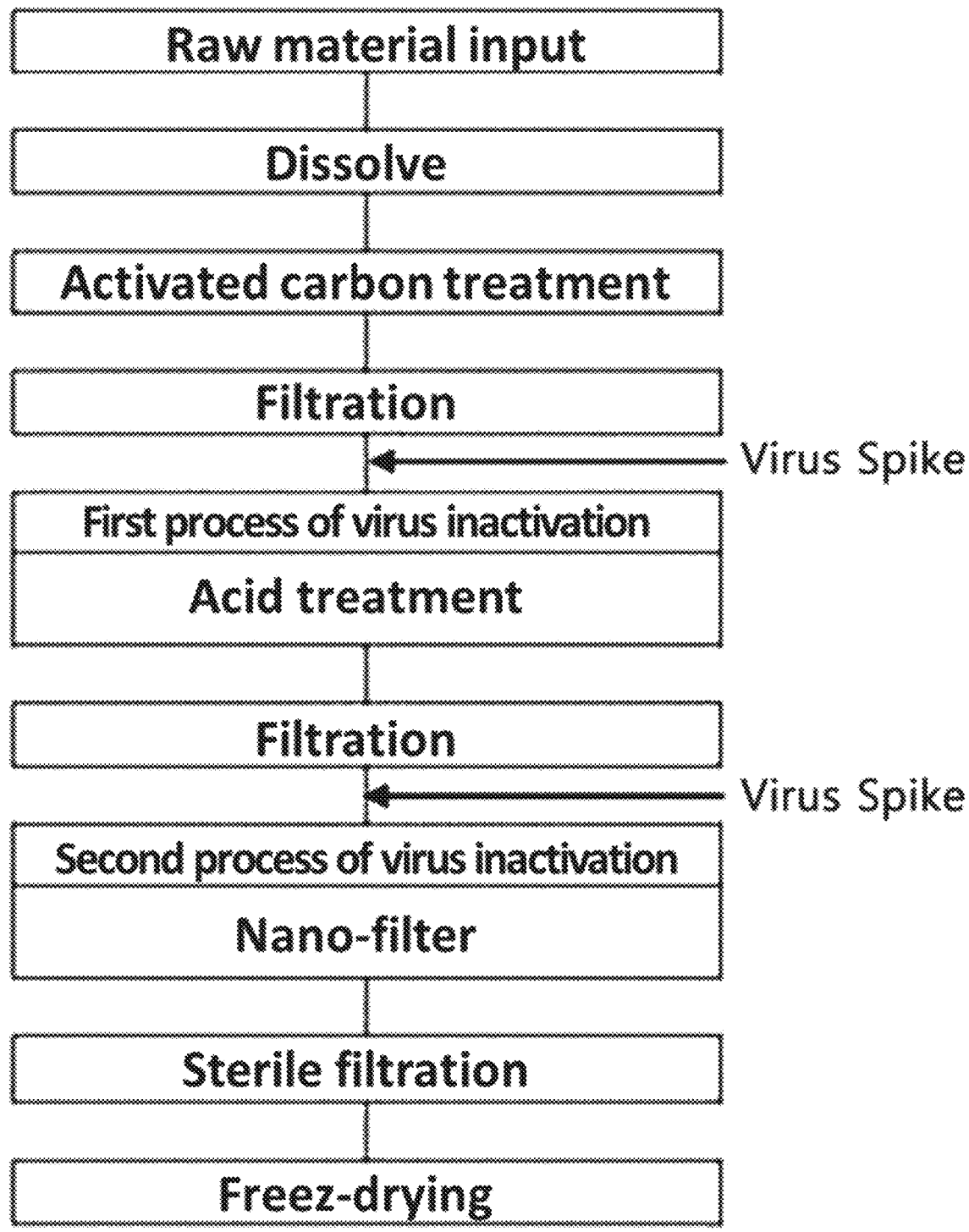
FIGS. 6(a) and (b) are schematic diagrams showing a verification procedure of the virus clearance process according to an embodiment of the present invention.
Figures 6B, 7:
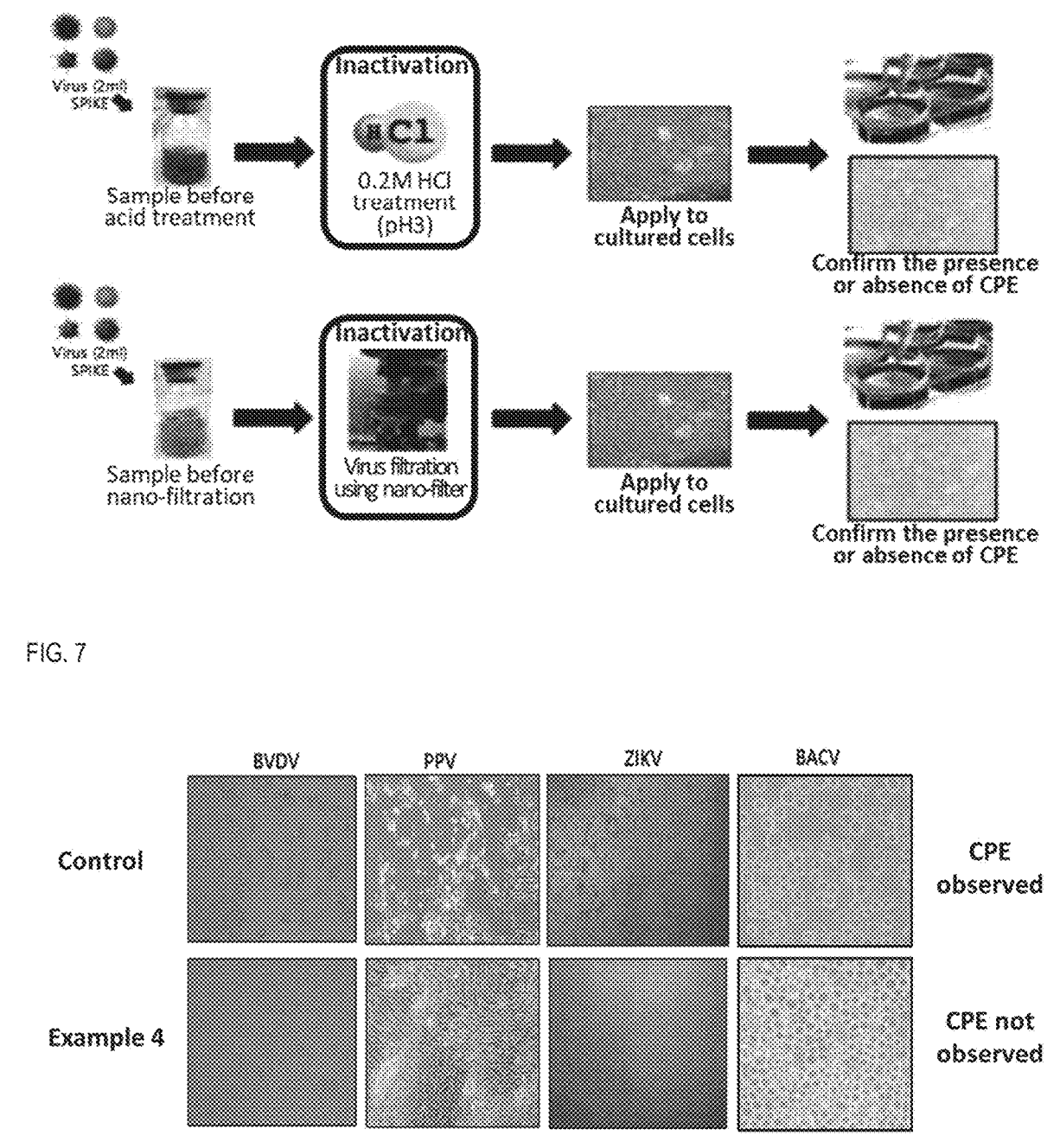

In order to verify the virus clearance process, with regard to the method for manufacturing bee venom along with the virus clearance process according to Example 4, as shown in FIGS. 6(a) and (b): 1) in the case where virus spikes were induced before acid treatment and the bee venom was treated with virus cultured cells after acid treatment; 2) virus spikes were induced before the nano-filtration process and the bee venom was treated with virus cultured cells after the nano-filtration process; and 3) virus spikes were induced before acid treatment and the bee venom was treated with virus cultured cells after the nano-filtration process, morphological changes (i.e., cytopathic effects (CPF)) were observed, and results thereof are shown in Table 7 and FIG. 7. At this time, the virus cultured cells used herein were Madin-Darby bovine kidney cells as BVDV cultured cells, porcine Kidney (PK15) cells as PPV cultured cells, VERO cells as ZIKA cultured cells, and SF9 cells as BACV cultured cells.

As shown in Table 7, 1) if subjected to an optimized acid treatment process, a virus reduction factor (Ri) in all of BVDV, PPV, ZIKV and BACV was in the range of 1.24 (±0.14) to 7.60 (±0.33) as the common log value, demonstrating that all viruses such as BVDV, PPV, ZIKV and BACV could be in activated. In particular, it could be seen that RNA viruses such as BVDV and ZIKV could be definitely inactivated. Further, 2) if subjected to the nano-filtration process, a virus reduction factor (Ri) in all of BVDV, PPV, ZIKV and BACV (virus reduction factor, Ri) was in the range of 4.45 (±0.41) to 7.53 (±0.53) as the common log value, demonstrating that all viruses such as BVDV, PPV, ZIKV and BACV could be definitely inactivated.

In other words, it was confirmed that a cumulative value of the virus reduction factors (Ri) in all viruses such as BVDV, PPV, ZIKV and BACV is within the range of 0.04 (±0.53) to 15.13 (±0.86) as common log values, demonstrating that all viruses such as BVDV, PPV, ZIKV and BACV could be sufficiently and definitely inactivated by combining acid treatment and a nano-filtration process.

TABLE 7

|  | Virus reduction factor (Ri) | | | |
| --- | --- | --- | --- | --- |
| Test item | BVDV | PPV | ZIKV | BACV |
| Acid treatment | ≥7.60 ± 0.33 | 1.59 ± 0.12 | ≥5.70 ± 0.46 | 1.25 ± 0.14 |
| Nano-filtration process | ≥7.53 ± 0.53 | ≥4.45 ± 0.41 | ≥6.45 ± 0.41 | ≥5.45 ± 0.41 |
| Combination of acid treatment and nano-filtration process | ≥15.1 ± 0.86 | ≥6.04 ± 0.53 | ≥12.15 ± 0.87 | ≥6.70 ± 0.55 |

Hereinafter, formulation examples of the composition containing the bee venom prepared according to the present invention will be described, but these examples are intended to describe the present invention in detail rather than limiting the same.

Formulation Example 1

Using the bee venom prepared according to Example 4, an injectable composition was prepared with the composition ratio shown in Table 8 below.

TABLE 8

| Component name | (Unit: mg) |
| --- | --- |
| Bee venom | 1.00 |
| Sodium chloride | 9.00 |

Formulation Example 2

Using the bee venom prepared according to Example 4, a tablet composition was prepared with the composition ratio shown in Table 9 below.

TABLE 9

| Component name | (Unit: mg) |
| --- | --- |
| Bee venom | 100 |
| Corn starch | 100 |
| Lactose | 100 |
| Magnesium stearate | 2 |

Formulation Example 3

Using the bee venom prepared according to Example 4, an ointment composition was prepared with the composition ratio shown in Table 10 below.

TABLE 10

| Component name | (Unit: wt. %) |
| --- | --- |
| Bee venom | 1.00 |
| Wax | 10.00 |
| Polysorbate | 5.00 |
| Hydrogenated castor oil | 2.0 |
| Sorbitansesquioleate | 0.5 |
| Vaseline oil | 5.0 |
| Liquid paraffin | 10.0 |

Formulation Example 4

Using the bee venom prepared according to Example 4, a sticky plaster type composition was prepared with the composition ratio shown in Table 11 below.

TABLE 11

| Component name | (Unit: wt. %) |
| --- | --- |
| Bee venom | 1.2 |
| Hexyleneglycol | 20.0 |
| Diethylamine | 0.7 |
| Polyacrylic acid | 1.0 |
| Sodium sulfite | 0.1 |
| Polyoxyethylenelauryl ether | 1.0 |
| Polyhydroxyethylenecetylstearylether | 1.0 |
| Paraffin oil | 2.5 |
| Caprylic acid ester | 2.5 |
| Polyethylene glycol | 3.0 |
| Deionized water | 100.0 |

Formulation Example 5

Using the bee venom prepared according to Example 4, a lotion type formulation composition was prepared with the composition ratio shown in Table 12 below.

TABLE 12

| Component name | (Unit: wt. %) |
| --- | --- |
| Bee venom | 3.00 |
| L-ascorbic acid-2-phosphoric acid salt | 1.0 |
| Water-soluble collagen (1% water-soluble solution) | 1.0 |
| Sodium citrate | 0.10 |
| Citric acid | 0.050 |
| Licorice extract | 0.20 |
| 1,3-butylene glycol | 3.00 |
| Purified water | Balance |

Formulation Example 6

Using the bee venom prepared according to Example 4, a cream type formulation composition was prepared with the composition ratio shown in Table 13 below.

TABLE 13

| Component name | (Unit: wt. %) |
| --- | --- |
| Bee venom | 1.00 |
| Polyethylene glycol monostearate | 2.00 |
| Self-emulsified monostearic acid glycerin | 5.00 |
| Cetyl alcohol | 4.00 |
| Squalane | 6.00 |
| Tri-2-ethylhexane glyceryl | 6.00 |
| Sphingoglycolipid | 1.00 |
| 1,3-butylene glycol | 7.00 |
| Purified water | Balance |

The above description of the present invention is for illustration only, and persons having ordinary knowledge in the technical field to which the present invention pertains ("those skilled in the art") may understand that the present invention can be easily modified into other specific forms without changing the technical spirit or essential features of the present invention. Therefore, it should be understood that the embodiments described above are illustrative in all respects and not restrictive.

The invention claimed is:

1. A method for purification of bee venom along with a virus clearance process, comprising: (a) preparing a bee venom solution containing bee venom; (b) firstly, inactivating virus by adjusting pH of the bee venom solution prepared in step (a) to 2.0 to 4.0 through acid treatment; and (c) secondly, removing the virus by filtering the pH-adjusted bee venom solution in step (b) through a nano-filter of 10 to 20 nm.

2. The method according to claim 1, wherein, in the step (a), the bee venom solution further includes at least one carbon-based adsorbent selected from the group consisting of activated carbon nanotubes and carbon fibers.

3. The method according to claim 1, wherein, through the acid treatment in step (b), viruses including bovine viral diarrheal disease virus (BVDV) or zika virus (ZIKV) are firstly inactivated.

4. The method according to claim 1, wherein the acid treatment in step (b) is performed by treating the bee venom solution with strong acid at a concentration of 0.1 to 1.0 M for 1 to 20 hours.

5. The method according to claim 1, wherein, in the step (b), the pH-adjusted bee venom solution maintains a melittin content of 45% by weight ("wt. %") or more.

6. The method according to claim 1, wherein, before the step (c), a step of filtering the pH-adjusted bee venom solution in the step (b) through a membrane filter of 0.05 to 1 μm is further included.

7. The method according to claim 1, wherein, through the nano-filter in the step (c), the virus including at least one selected from the group consisting of bovine viral diarrhea virus (BVDV), zika virus (ZIKV), porcine parvovirus (PPV) and baculovirus (BACV) is secondarily removed.

8. The method according to claim 1, wherein the nano-filter in the step (c) is made of polyethersulfone (PES).

9. The method according to claim 1, wherein the bee venom solution filtered in step (c) has a filtration rate of 600 mL/hr or higher or a yield of 60% or higher while maintaining both melittin and protein contents of 45 wt. % or more.

10. The method according to claim 1, further comprising, after step (c):
   (d) filtering the bee venom solution filtered in step (c) through a 0.1-1 μm sterile filter, after step (c); and
   (e) freeze-drying the bee venom solution filtered in step (d).

11. A pharmaceutical composition for preventing or treating inflammatory diseases, comprising bee venom prepared by the method according to claim 1.

12. A cosmetic composition for preventing or treating inflammatory diseases, comprising bee venom prepared by the method according to claim 1 as an active ingredient.

* * * * *